United States Patent [19]
Copeland

[11] 4,303,410
[45] Dec. 1, 1981

[54] LIGHT BURST ACTIVITY ANALYZER

[75] Inventor: Hugh D. Copeland, Chula Vista, Calif.

[73] Assignee: The United States of America as represented by the Secretary of the Navy, Washington, D.C.

[21] Appl. No.: 203,003

[22] Filed: Nov. 3, 1980

[51] Int. Cl.³ .................... G01N 33/18; G01N 21/76
[52] U.S. Cl. .............................. 23/230 R; 250/361 C; 364/498; 422/52; 435/808
[58] Field of Search .................... 23/230 R, 230 B; 422/52, 62; 250/361 R, 361 C, 369; 364/497, 498; 435/808; 356/317, 318

[56] References Cited

U.S. PATENT DOCUMENTS

| | | | |
|---|---|---|---|
| 3,520,660 | 7/1970 | Webb | 23/253 |
| 3,749,929 | 7/1973 | Wooten | 422/52 X |
| 3,756,920 | 9/1973 | Kelbaugh et al. | 422/52 X |
| 3,797,999 | 3/1974 | Witz et al. | 250/361 C |
| 3,832,532 | 8/1974 | Praglin et al. | 235/151.3 |
| 3,836,262 | 9/1974 | Yata et al. | 356/226 |
| 3,849,653 | 11/1974 | Sakaide et al. | 250/361 C |
| 3,902,052 | 8/1975 | Amar et al. | 364/497 |
| 3,919,050 | 11/1975 | Curby | 195/103.5 R |

Primary Examiner—Ronald Serwin
Attorney, Agent, or Firm—R. S. Sciascia; Ervin F. Johnston; James O. Skarsten

[57] ABSTRACT

Apparatus is provided for analyzing the structure of light burst activity which is generated by a particular light source, such as a group of bioluminescent organisms. The apparatus includes a photon detector for detecting discrete photons of light occurring proximate to the source during each sampling time in a series of sampling times, and further includes a counter coupled to the photon detector for providing successive photon counts, a photon count being the number of discrete photons detected by the photon detector during one of the sampling times. A pulse height analyzing device is coupled to the counter for providing a distribution of the photon counts over the sampling time series.

14 Claims, 3 Drawing Figures

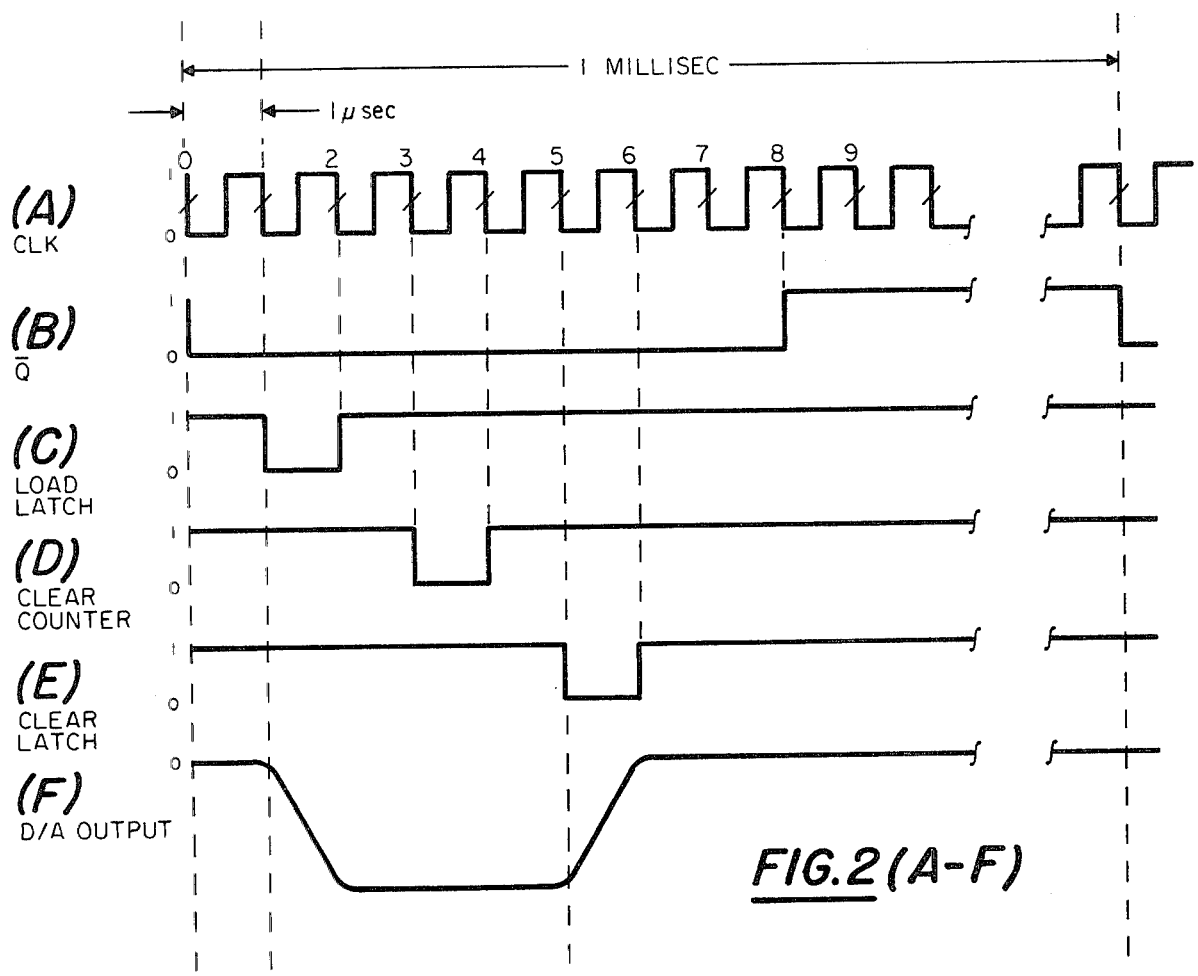
*FIG.2(A-F)*
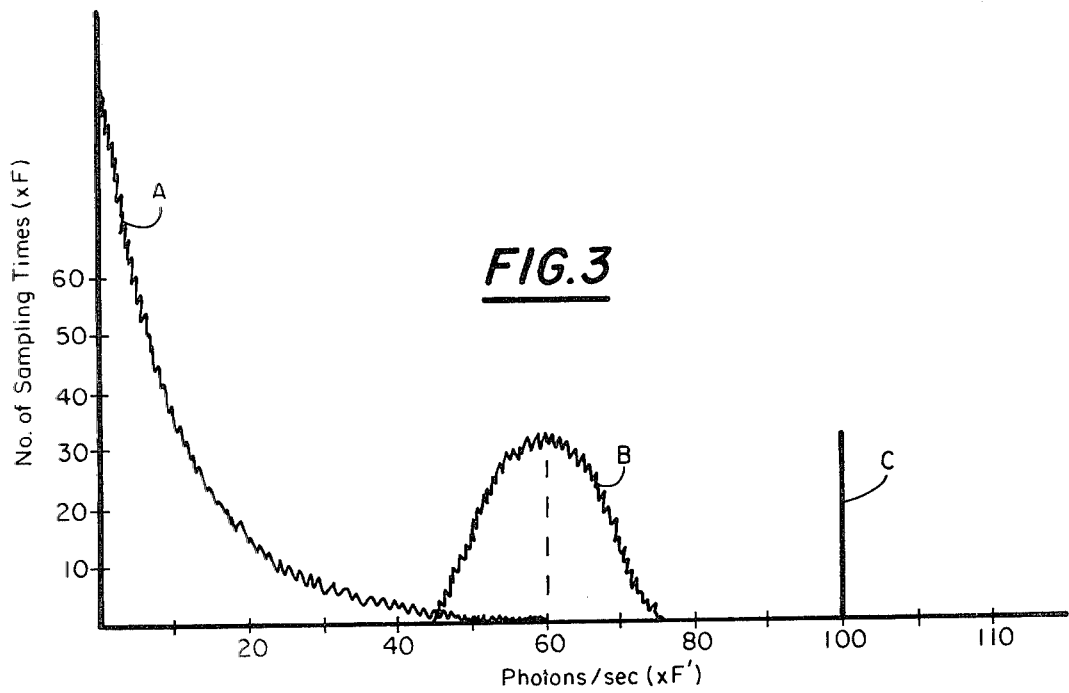
*FIG.3*

LIGHT BURST ACTIVITY ANALYZER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The invention disclosed and claimed herein generally pertains to the field of techniques and apparatus for analyzing light burst activity, that is, the emission of light in the form of discrete bursts, pulses or flashes, which are of extremely short duration. More particularly, the invention pertains to the above field wherein analysis is accomplished by detecting and counting discrete light photons produced by a light burst source during successive time intervals in a series of intervals, and then providing a probability distribution function of photon counts over the series.

A source of light burst activity which is of special interest is the bioluminescent life, and particularly the microorganic life, which is found in natural bodies of seawater. One reason for such interest results from proposals which are presently being made for a system which is intended to communicate through an ocean body by means of laser light signals. Because light signals passing through a seawater environment are subjected to a high degree of attenuation, the effects of bioluminescence on signal reception at a receiver in the environment may be very significant.

In studying the phenomenon of bioluminescence in seawater, certain questions have been posed. One such question is whether the emission of a light burst by one bioluminescent creature in seawater in some way causes nearby creatures to emit light, or whether adjacent creatures act independently of one another. Other questions are related to the structure or pattern of light emission, such as whether light emissions occur continuously or are separated by time intervals, or whether the intensity of light bursts is continuous or variable over time.

The applicant, through his invention, discloses a tool which is considered to be extremely useful for providing information pertinent to the above questions. However, the applicant does not intend to limit his invention to applications related to the analysis of bioluminescent light emissions. It is anticipated that the invention could also be useful in analyzing the structure of sparking activity, or virtually any other sort of light emitting activity in which emissions are of very short duration, emission occurring over a period of time.

SUMMARY OF THE INVENTION

In the present invention, apparatus is provided for analyzing the structure of light burst activity which occurs over a period of time. The apparatus includes means for detecting discrete photons generated by successive light bursts during each sampling time in a series of sampling times, and further includes means coupled to the photon detecting means for providing successive photon counts. Each of the photon counts comprises the number of discrete photons which are detected by the photon detecting means during one of the sampling times. Data processing means coupled to the counting means provides a distribution of the photon counts, or photon count rate, over the series of sampling times, such distribution being the number of sampling times during which various photon rates are registered by the counting means.

In a preferred embodiment of the invention, the counting means comprises a digital counter, and the data processing means includes an analog pulse height analyzer. A digital to analog converter is coupled between the digital counter and the pulse height analyzer, and digital latches and timing circuitry are provided to synchronize the operation of the counter, converter and pulse height analyzer during successive sampling times. Such preferred embodiment may be very usefully employed to analyze light bursts generated by bioluminescent microorganisms in an ocean or other seawater environment, light bursts generated thereby lasting for times which are on the order of milliseconds. A photo multiplier tube may be employed as the detecting means in such preferred embodiment, and the distribution provided by the pulse height analyzer device may be visually displayed, in real time.

OBJECTS OF THE INVENTION

An object of the present invention is to provide a new and improved tool for studying or analyzing light burst activity, that is, of patterns of light emission occurring over a period of time, wherein each discrete emission is of very short duration.

Another object is to determine whether light is being emitted continuously by a particular light burst source, or whether discrete dark times, or periods of nonemission, occur between bursts.

Another object is to determine whether light bursts emitted by a particular source are of continuous or of varying intensity.

Another object is to analyze the structure of light burst activity, wherein individual bursts have time durations which are on the order of milliseconds or less.

Another object is to analyze the structure of light burst activity which is generated by a source comprising the bioluminescent microorganisms which are present in a selected environment, such as a quantity of seawater.

Another object is to provide a capability to distinguish between the occurrence of a single one of such bursts of high intensity from the near-simultaneous occurrence of a number of such bursts which are of much lower intensity.

Another object is to provide a real time display of data from which various characteristics of light bursts emitted by a particular source may be determined.

Other objects and many of the attendant advantages of this invention will be readily appreciated as the same becomes better understood by reference to the following detailed description, when considered in connection with the accompanying drawings.

BRIEF DESCRIPTION OF THE DRAWINGS

FIG. 2 is a timing diagram useful for understanding the operation of the embodiment of FIG. 1.

FIG. 3 is a graphic representation of data which may be generated by the embodiment of FIG. 1.

DETAILED DESCRIPTION OF THE PREFERRED EMBODIMENT

Figure 1:
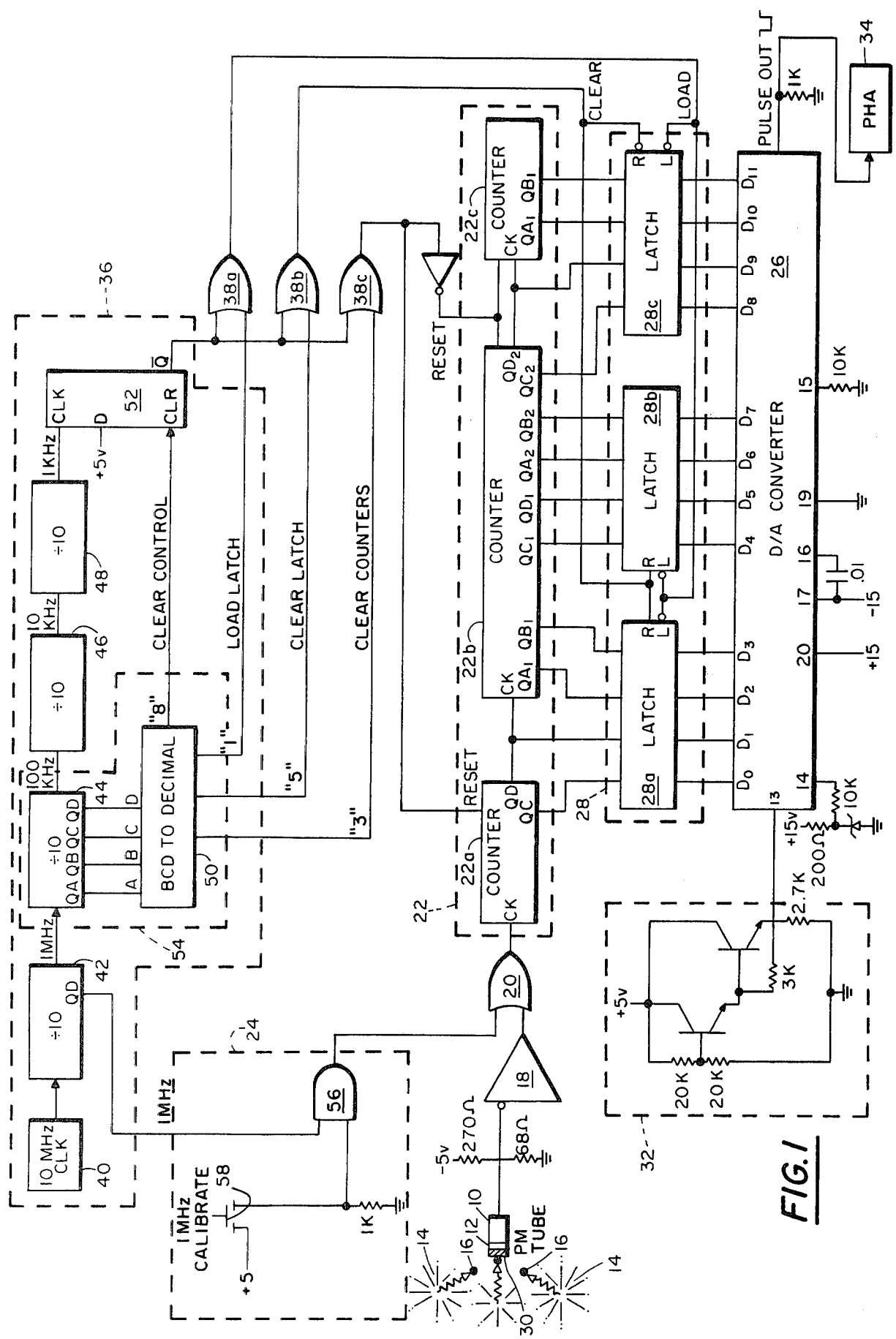
FIG. 1 is a schematic view showing an embodiment of the invention.

Referring to FIG. 1, there is shown a photo multiplier tube 10 having a light sensitive surface 12 which is oriented toward light bursts 14. Light bursts 14 are successively generated by a particular source, such as bioluminescent microscopic life in a quantity of seawater. Photo multiplier tube 10 may be adapted for immersion in a natural body of water to observe bioluminescent activity therein, or alternatively, may be structured to observe bioluminescence in a quantity of seawater which has been brought into a tank or laboratory situation. Phototube 10 is selected from a number of presently available photomultiplier devices, according to the operating characteristics required therefore, and usefully comprises a device which operates at the speeds and voltage levels of the ECL digital logic family.

Discrete bursts of light 14 generated by bioluminescent creatures have time durations which are on the order of milliseconds. Each time a burst occurs, photons 16 are generated, some of which are projected toward light sensitive surface 12 of phototube 10 and which impinge thereupon. Each photon 16 impinging upon surface 12 causes a discrete pulse to be generated by phototube 10 and to be coupled through a translator circuit 18 and an OR gate 20 to a digital counter 22. Translator 18 is a standard device for providing an interface between digital equipment of different logic families, and is necessary where, for example, phototube 10 operates at ECL voltage levels and speed, while counter 22 is a digital component operating at the levels and speed of TTL logic. OR gate 20 is employed to selectively couple calibration circuit 24 to counter 22, calibration circuit 24 being described hereinafter in conjunction with FIG. 3.

Referring further to FIG. 1, there is shown counter 22 comprising three interconnected digital counter elements 22a–c, element 22a usefully comprising an integrated circuit element conventionally referred to as an IC 74S197, and elements 22b and 22c each comprising an integrated circuit element referred to as an IC74393. By interconnecting elements 22a–c as shown in FIG. 1, a counter 22 is provided which is capable of registering up to $2^{12}$ counts, a count being registered, as aforementioned, each time a photon 16 impinges upon light sensitive surface 12 of phototube 10.

It has been found that data which is very useful for bioluminescent activity may be provided by operating counter 22 in successive cycles, or sampling times, which are on the order of one millisecond in length. At the commencement of a sampling time, counter 22 is in a cleared condition, or set to zero. During the sampling time, counter 22 counts successive photons impinging upon light sensitive surface 12 of phototube 10, and at the conclusion of the sampling time, a digital number representing the total number of photons counted during the sampling time is shifted from counter 22 to digital to analog (D/A) converter 26, through latch 28. It will be readily apparent that the number of photons counted by counter 22 during a sampling time is dependent upon the number of bursts 14 occurring thereduring, as well as on the intensity of light emitted by respective bursts. In addition, if it is desired to monitor only the emission of light which is in a particular wavelength range, a filter 30 may be fitted over surface 12, which prevents passage of all photons except those having a wavelength within the particular range. If a filter 30 is used, the count of counter 22 will be dependent on the amount of light emitted by bursts 14 which is in the wavelength range of the filter.

Latch 28 usefully comprises three latch elements 28a–c, each commercially denoted as an IC74197, and D/A converter 26 usefully comprises a D/A converter known commercially as AM 6012. FIG. 1 shows pin 13 of D/A converter 26 connected to an interfacing circuit 32, and further shows pin 14 through pin 20 coupled to various other circuit components and voltage sources. It will be apparent to one of skill in the art that such components and sources are necessary in order to interface a D/A converter device AM 6012 with TTL logic components such as counter 22 and latch 28.

Upon receiving a sampling time count from counter 22, converter 26 generates a pulse having a height which is proportional to the count, the pulse being coupled to a pulse height analyzer 34. Analyzer 34 comprises a device well known in the art, such as a multichannel analyzer manufactured by D. Davidson Corp., and is capable of presenting data representing the heights of pulses generated by converter 26 over successive millisecond sampling times in a very useful form. Each pulse of a particular height or amplitude received by the analyzer is inputted to a corresponding bin or channel, so that at the conclusion of a series of sampling times, pulse height analyzer 34 is able to provide a probability distribution function of photon count rate for a particular source of bursts 14. The use of such probability distribution function to determine certain characteristics pertaining to particular light burst emissions are described hereinafter in greater detail, in conjunction with FIG. 3.

In order to insure proper operation of converter 26 and analyzer 32, the entire count registered by counter 22 during a sampling time must be coupled to converter 26 during a period of time which is infinitesimal in comparision with a 1 millisecond sampling interval. Also, converter 26 must be prevented from receiving any inputs except the total photon counts of successive sampling intervals. Consequently, a timing circuit 36 and OR gates 38a–b are provided, to properly synchronize the operation of counter 22, latch 28 and converter 26. Timing circuit 36 includes a 10 megahertz clock 40, and further includes frequency dividers 42, 44, 46, and 48, each having the capability of generating an output frequency which is one-tenth its input frequency. By configuring frequency dividers 42, 44, 46 and 48 as shown in FIG. 1, the outputs thereof are respectively 1 megahertz. 100 kilohertz, 10 kilohertz, and 1 kilohertz.

In addition to frequency dividers 42–48, timing circuit 36 includes a BCD to decimal converter 50 and a "D" flip-flop 52, which is clocked by the 1 kilohertz output of frequency divider 48. Frequency divider 44 and converter 50 are interconnected to form a counter 54, which cyclically counts to 10 in increments of 1 microsecond, the time period of the 1 MHz signal received by frequency divider 44. Each microsecond count is outputted in binary coded decimal (BCD) form on terminals QA–QD, which are respectively coupled to input terminals A–D of converter 50. Converter 50 has inverted output terminals "1"–"10," each of which is at logic 0 when the count to which it corresponds is being generated by divider 44, and which is otherwise maintained at logic 1. Inverted output terminals "1," "5," and "3" are coupled as inputs to OR gates 38–38c, respectively, the other input to each OR gate comprising the output of the $\overline{Q}$ terminal of "D" flip-flop 52. Flip-flop 52 is cleared by a logic 0 from inverted output terminal "8" of converter 50.

Referring now to FIG. 2 in conjunction with FIG. 1, there is shown, in row "A," the 1 megahertz output of divider 42 coupled to divider 44, to incrementally update counter 54 at intervals of 1 microsecond as aforementioned. Referring to row "B," there is shown the output of the $\overline{Q}$ terminal of "D" flip-flop 52 which, as aforementioned, is clocked by the 1 kilohertz signal generated by frequency divider 48. Consequently, at the beginning of each sampling time in a series of 1 millisecond sampling times, output $\overline{Q}$ of "D" flip-flop 52 goes to logic 0.

Referring to row "C," there is shown the output of inverted terminal "1" of converter 50, which is at logic 0 during the first count of counter 54, during each 10-count cycle thereof. Since output $\overline{Q}$ of flip-flop 52 is also at logic 0 during the first count of a 10-count cycle beginning at the commencement of a millisecond sampling time, a logic 0 is coupled from OR gate 38a to the load terminal L of each of the latch elements 28a–c of latch 28, for the duration of such first count. Each latch element 28a–c is structured to respond to a logic 0 at its load terminal to load data coupled thereto. Consequently, 1 microsecond after the commencement of a sampling time, the output lines of counter 22, which are coupled to corresponding inputs of latch 28, are coupled through latch 28 to respective input terminals of D/A converter 26. The contents of counter 22 at such time, representing the number of photons sensed by phototube 10 during the previous sampling time, are thereby received by converter 26.

Referring to rows "D" and "E" of FIG. 2, there are shown the third and fifth counts of counter 54, respectively, which are generated following the commencement of a sampling time. Therefore, 2 microseconds after OR gate 38a generates a signal which causes data in counter 22 to be loaded into converter 26, OR gate 38c generates a logic 0 which is coupled to counter 22 to clear or reset respective counter elements 22a–c. 2 microseconds after counter 22 is cleared, latch 28 is cleared by a logic 0 from OR gate 38b, so that data from counter 22 may no longer pass therethrough to converter 26. Referring once more to row "B" of FIG. 2, it is shown that 3 microseconds after latch 28 is reset, and 8 microseconds after the commencement of the 1 millisecond sampling time, the eighth count of counter 54 clears flip-flop 52, returning the output of terminal $\overline{Q}$ thereof to logic 1 until the commencement of the following sampling time.

It will be readily apparent that by regulating the operation of counter 22 and latch 28 as described above, over successive sampling times, counter 22 is enabled to count photons received by phototube 10 during the entire length of each sampling time, except for a negligible dead time period. Such period occurs during the 3 microsecond interval between the loading of latch 28 and clearing of counter 22. In addition, by synchronously operating counter 22 and latch 28 in the above described manner, no data may be coupled to converter 26 except data representing the entire photon count registered by counter 22 during a sampling time.

Referring to row "F" of FIG. 2, there is shown the output of D/A converter 26, comprising an analog pulse which is generated by converter 26 over a 4–5 microsecond period after data is received thereby from counter 22. The amplitude and shape of the output pulse of converter 26 is a direct analog representation of the number of photons impinging upon phototube 10 during the preceding sampling time, and is coupled to pulse height analyzer 34, as aforementioned.

As is well known in the art, a pulse height analyzer is a device which receives data in the form of an analog pulse. Each time a pulse of a particular value is received by the analyzer, an entry is registered in a channel which corresponds to the particular value. At the conclusion of the sampling time period, the pulse height analyzer provides a probability distribution function which indicates the probability that a particular value of the quantity of interest will occur over a time period.

It will be readily apparent that a pulse height analyzer device may be employed to provide information from which certain characteristics of light bursts 14 may be determined. When used for such purpose, each data sample coupled to analyzer 34 comprises an analog pulse, as forementioned, which represents the number of photons sensed by phototube 10 during a 1 millisecond sampling time. At the conclusion of a selected number of sampling times, the pulse height analyzer provides a probability distribution function (PDF) which is determined by the structure of the light bursts or emissions 14 which are being monitored by phototube 10. Pulse height analyzer 34 very usefully includes a printout or a CRT display device for graphically representing a PDF derived from photon emission data provided over a long series of sampling times, right after the conclusion of such series, or in real time.

Referring to FIG. 3, there are shown curves A and B which are respectively generated by pulse height analyzer 34 to represent probability distribution functions associated with different possible patterns of light burst activity under observation by phototube 10. The horizontal dimension of FIG. 3 is scaled in photons per second, multiplied by a selected scaling factor F, which is the sampled quantity of interest which is received by analyzer 34, i.e., photons per unit time. The vertical dimension of FIG. 3 indicates the number of sampling times, in a series of sampling times, during which a specific value of photon count rate is coupled to analyzer 34, the vertical dimension being scaled by a selected factor F.

Referring to curve A of FIG. 3, a probability distribution function is shown which indicates that during nearly all of the millisecond sampling times of a sampling time series, very few photons have been detected by phototube 10. At the same time, it may appear to the unaided human eye that light has been continuously emitted over the sampling time series. In such case, the conclusion must be drawn that light burst activity providing the data from which curve A is constructed must occur in the form of extremely brief pulses, separated by discrete intervals of dark time, or nonemission. The sharper the curve A becomes, the longer the times of nonemission must be, to increase the comparative numbers of sampling times during which phototube 10 receives only small numbers of photons.

Referring to curve B of FIG. 3, there is shown a Gaussian or bell-shaped distribution of photon counts, which is well known by those of skill in the art of probability distribution function analysis to represent samples of data which are substantially constant in both amplitude and time. If phototube 10 were to monitor sunlight, for example, the curve generated by analyzer 34 in response to data coupled thereto would have the shape of curve B. Consequently, if a PDF having the shape of curve B is derived from data generated by particular light burst activity 14, it may be concluded that the intensity or amplitude of emitted light is constant over time. It may further be concluded that while individual bursts may be of very short duration, some burst or bursts are occurring at all times over a series of sampling times. The height of curve B is determined by the total number of sampling times in the series. For example, if photons generated by light bursts 14 are counted for 1 millisecond sampling times for a period of two hundred seconds, curve B would be derived from data provided by 200,000 sampling times. The positioning of curve B on the horizontal dimension is determined by the comparative intensity of light emission.

Referring to curve C of FIG. 3, there is shown a probability distribution function which is generated by calibration circuit 24, in order to calibrate the horizontal scale of the graphic display of analyzer 34. Referring once more to FIG. 1, there is shown the QD output of frequency divider 42 employed as a first input to AND gate 56 of calibration circuit 24. Consequently, one of the inputs to AND gate 56 comprises a stream of digital pulses of 1 megahertz frequency. When a calibration select switch 58 is deactivated, the second input to AND gate 56 is logic 0. However, when calibration select switch 58 becomes activated, the second input of AND gate 56 goes to logic 1, so that a series of digital pulses of 1 megahertz frequency are coupled from AND gate 56 to OR gate 20, and therethrough into counter 22. The counts registered in counter 22 by successive pulses from AND gate 56, during successive sampling times, are coupled to pulse height analyzer 34 as successive data samples.

Obviously, many modifications and variations of the present invention are possible in the light of the above teachings. It is therefore understood that within the scope of the disclosed inventive concept, the invention may be practiced otherwise than as specifically described.

What is claimed is:

1. Apparatus for analyzing the structure of light burst activity which occurs over a period of time, said apparatus comprising:
    means for detecting discrete photons generated by successive light bursts of said activity during each sampling time in a series of sampling times;
    means coupled to said photon detecting means for providing successive photon counts, each of said photon counts comprising the number of discrete photons detected by said photon detecting means during one of said sampling times; and
    data processing means coupled to said counting means for providing the distribution of said photon counts over said series of sampling times.

2. The apparatus of claim 1 wherein the source of said light bursts comprises a number of bioluminescent microorganisms in a selected environment, and wherein:
    said photon detecting means and said counting means comprise means for respectively detecting and counting discrete photons during sampling times which are on the order of milliseconds; and
    said data processing means comprises a pulse height analyzing device.

3. The apparatus of claim 1 wherein:
    said counting means comprises a digital counting means; and
    said data processing means includes an analog pulse height analyzing device.

4. The apparatus of claim 3 wherein said data processing means includes:
    digital to analog converter means for coupling a succession of analog pulses to said pulse height analyzing device, each of said pulses representing one of said photon counts; and
    control means for coupling a photon count provided during a given one of said sampling times to the input of said converter means at the commencement of the sampling time which directly follows said given sampling time in said series.

5. The apparatus of claim 4 wherein said control means comprises:
    digital latch means coupled between the output of said counting means and the input of said converter means; and
    timing means coupled to said counting means and said latch means for operating said latch means in selected synchronous relationship with said counting means during each of said sampling times.

6. The apparatus of claim 5 wherein the source of said light burst activity comprises the bioluminescent organisms present in a seawater environment, and wherein said timing means comprises:
    means for enabling said counting means to count photons detected by said detection means over a sampling time which is on the order of milliseconds, except for a data loading interval which is on the order of microseconds, in order to provide one of said photon counts; and
    means for operating said latch means to couple data representing one of said photon counts to said converter means from said counter means during one of said loading intervals, and to prevent data from being coupled to said converter means except during said data loading intervals.

7. The apparatus of claim 6 wherein:
    said timing means comprises cyclical counting means for generating a first signal which commences one of said sampling times, for generating a second signal which commences a data loading interval during one of said sampling times, and for generating a third signal which concludes one of said data loading intervals.

8. The apparatus of claim 4 wherein:
    said pulse height analyzing device includes display means for providing a graphical representation of a probability distribution function at the conclusion of said series of sampling times, said function being determined by said structure of said light burst activity.

9. The apparatus of claim 8 wherein said display means includes:
    a horizontal scale for representing various values of photon counts provided by said counting means during said series of sampling times; and
    a vertical scale for representing the number of sampling times in said series during which a particular value of photon count is provided.

10. The apparatus of claim 9 wherein:
    said apparatus includes a circuit coupled to the input of said counting means for selectively calibrating said horizontal scale of said pulse height analyzer device.

11. The apparatus of claim 4 wherein:
    said photon detecting means comprises a photomultiplier tube adapted for immersion in seawater.

12. The apparatus of claim 4 wherein:

said photon detection means comprises means for detecting only discrete photons generated by said light burst activity which have wavelengths inlcuded in a preselected range of wavelengths.

13. A method for analyzing the structure of light burst activity which occurs over a period of time, said method comprising the steps of:
   detecting discrete photons generated by successive light bursts during each sampling time in a series of sampling times;
   counting the number of photons detected during a given sampling time to provide a photon count for said given sampling time; and
   coupling each of said sampling times to a pulse height analyzing device to generate a probability distribution function at the conclusion of said sampling time series, said function indicating the probability that a particular photon count value will be generated by said light burst activity during a specified period of time.

14. The method of claim 13 wherein said light burst activity is generated by bioluminescent microorganisms contained in a quantity of seawater, and wherein:
   said counting step comprises the step of counting the number of photons which are detected during each sampling time in a series of sampling times which are on the order of 1 millisecond.

* * * * *